United States Patent [19]
Vincent et al.

[11] Patent Number: 5,098,888
[45] Date of Patent: Mar. 24, 1992

[54] NEW HETEROCYCLIC TRIPEPTIDE COMPOUNDS

[75] Inventors: Michel Vincent, Bagneux; Georges Remond, Versailles; Bernard Portevin, Elancourt; Yolande Herve, Puteaux; Jean Lepagnol, Chatou; Catherine Biton, Nanterre, all of France

[73] Assignee: Adir Et Compagnie, Courbevoie, France

[21] Appl. No.: 536,193

[22] Filed: Jun. 11, 1990

Related U.S. Application Data

[63] Continuation-in-part of Ser. No. 384,429, Jul. 24, 1989, abandoned.

[30] Foreign Application Priority Data

Jun. 29, 1989 [FR] France ................... 89 08672

[51] Int. Cl.[5] ................. A61K 37/02; C07K 5/08
[52] U.S. Cl. ..................... 514/18; 514/19; 530/331
[58] Field of Search .............. 530/331; 514/18, 19

[56] References Cited

U.S. PATENT DOCUMENTS

| | | | |
|---|---|---|---|
| 4,060,603 | 11/1977 | Morgan et al. | 530/331 |
| 4,748,155 | 5/1988 | Sisto et al. | 530/331 |
| 4,814,342 | 3/1989 | Hoover et al. | 530/331 |
| 4,826,814 | 5/1989 | Sawayama et al. | 530/331 |
| 4,956,344 | 9/1990 | Fossli et al. | 530/331 |

*Primary Examiner*—Lester L. Lee
*Attorney, Agent, or Firm*—Gordon W. Hueschen

[57] ABSTRACT

The invention relates to the compounds of general formula (I):

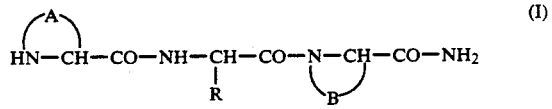

in which:
- A represents, with the carbon and nitrogen atoms to which it is linked, a cycloamide group,
- B represents, with the carbon and nitrogen atoms to which it is linked, a saturated polycyclic structure,
- R represents a hydrogen atom, a lower alkyl group or a substituted or unsubstituted 4-imidazolylmethyl group, their diastereoisomers, enantiomers and epimers, as well as their addition salts with a pharmaceutically acceptable acid.

Medicinal products.

17 Claims, No Drawings

NEW HETEROCYCLIC TRIPEPTIDE COMPOUNDS

Cross-reference in related applications: this is a continuation-in-part of our copending application Ser. No. 07/384,429 filed July 24, 1989 now abandoned.

The present invention relates to new peptide compounds, to a process for preparing them and to pharmaceutical compositions containing them.

Among natural tripeptides, some tripeptides having a cycloamide structure exert advantageous central effects, in particular with respect to cholinergic neurotransmission. This is the case, in particular, with TRH (thyrotropin-releasing hormone) of structure pyroglutamylhistidylprolinamide, which is capable of counteracting the fall in acetyl choline synthesis induced experimentally by narcosis. It is also capable of boosting the central cholinergic symptoms induced by cholinergic agonists.

However, on account of its metabolism, TRH is rapidly inactivated in the body. Similarly, it is inactivated when taken orally as a result of its virtually instantaneous degradation at gastric level.

Other tripeptides have been described (Patents FR 2,187,155, 2,287,916, 2,266,515 and 2,345,448), in which the pyroglutamyl residue is replaced by another heterocyclic carboxylic acid residue and which possess anticonvulsant and antidepressant properties. Finally, Patent FR 2,585,709 describes peptides in which the prolinamide residue is replaced by a saturated bicyclic structure and which are capable of stimulating cyclic AMP synthesis in the cerebral tissue. However, these compounds have virtually no activity when administered orally.

The compounds of the present invention, in which the prolinamide residue is replaced by a novel saturated bicyclic structure, have been shown to be very advantageous, in particular as regards their properties of mimicking and exacerbating the activities of TRH, of which they constitute analogues as demonstrated in a study performed by autoradiography. However, the level of activity of the derivatives of the invention is markedly greater than that of TRH itself.

Furthermore and surprisingly, the novel saturated bicyclic structure characteristic of the compounds of the invention renders these compounds active orally, in contrast to the previously known derivatives of related structure. This feature makes the compounds of the invention much more suitable for therapeutic use than those of related structure described in the prior art.

The invention relates more especially to new compounds having a cycloamide structure corresponding to the general formula (I):

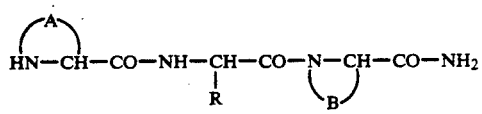

in which:
A represents, with the nitrogen and carbon atoms to which it is linked:
  a 2-oxo-5-pyrrolidinyl group,
  a 2-oxo-6-piperidyl group,
  a 2,6-dioxo-1,2,3,6-tetrahydro-4-pyrimidinyl group,
  a 2-oxo-4-thiazolidinyl group,
  a 2-oxo-4-azetidinyl group,
  a 1oxo-1,2,3,4-tetrahydro-3-isoquinolyl group,
B represents, with the nitrogen and carbon atoms to which it is linked, a saturated polycyclic structure selected from 2-azabicyclo[2.2.1]heptane or 1,4-di(-linear or branched lower alkyl)-2-azabicyclo[2.2.2]-octane,
R represents a hydrogen atom, a linear or branched lower alkyl group or a (4-imidazolyl)methyl group optionally substituted on one of the nitrogen atoms with a linear or branched lower alkyl radical, the term lower indicating that the groups thus qualified contain from 1 to 6 carbon atoms, their enantiomers, diastereoisomers and epimers, as well as their addition salts with a pharmaceutically acceptable acid.

Among pharmaceutically acceptable acids, hydrochloric, sulphuric, tartaric, maleic, fumaric, oxalic, methanesulphonic and camphoric acids, and the like, may be mentioned without implied limitation.

The invention also encompasses the process for preparing the compounds of formula (I), characterized in that the amine function of an amino acid of formula (II), the isomers of which have optionally been separated by a conventional separation technique:

in which B has the same meaning as in the formula (I), is protected with a protective radical (P) such as tert-butoxycarbonyl (tBOC) or benzyloxycarbonyl (Z), by the action of a suitable reagent, to lead to a compound of formula (III):

in which B and P have the same meaning as above, which is reacted, at a temperature of between $-15°$ and $0°$ C., in the presence of triethylamine, with ethyl chloroformate and then ammonia solution, to lead to a compound of formula (IV):

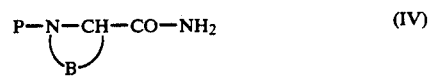

in which B and P have the same meaning as above, which is deprotected by a suitable process such as, for example, the action of gaseous hydrochloric acid in an anhydrous solvent such as dioxane or ethyl acetate in the case where P=tBOC or by catalytic hydrogenation in the case where P=Z, to lead to a compound of formula (V):

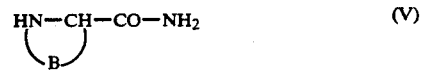

in which B has the same meaning as in the formula (I), the isomers of which are separated, if so desired, by a conventional separation technique, which is coupled with a second protected amino acid of formula (VI) according to the peptide coupling technique described by W. KONIG and R. GEIGER (Ber. 103, 788, 1970):

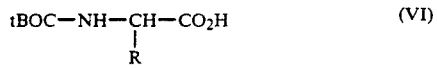

in which R has the same meaning as in the formula (I), to lead to a compound of formula (VII):

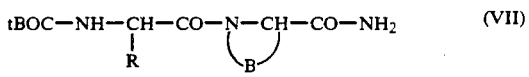

in which R and B have the same meaning as in the formula (I),
the diastereoisomers or enantiomers of which are separated, if so desired, by a conventional separation technique,
which is then deprotected by the action of gaseous hydrochloric acid in an anhydrous solvent such as, for example, dioxane or ethyl acetate, to lead to a compound of formula (VIII):

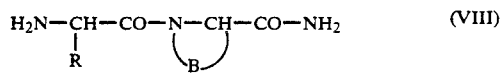

in which R and B have the same meaning as in the formula (I),
which is coupled with a third amino acid, optionally protected, of formula (IX), according to the peptide coupling technique described above:

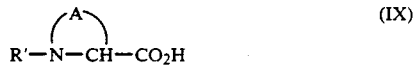

in which R' is a hydrogen, or a protective group such as, for example, a benzyloxycarbonyl (Z),
or with an ester of this optionally protected amino acid, to lead:
either to a compound of formula (I) in the case where R' is a hydrogen,
or to a compound of formula (X):

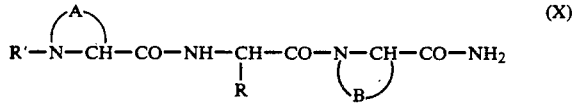

in the case where R' is a protective group, R and B having the same meaning as in the formula (I), which is deprotected by a deprotection technique, such as, for example, a catalytic hydrogenation, to lead to a compound of formula (I), which is converted, if so desired, to its addition salts with a pharmaceutically acceptable acid or separated into its isomers according to a conventional separation technique, which are then, if necessary, salified with a pharmaceutically acceptable acid.

The compounds of formula (II) in which B represents, with the nitrogen and carbon atoms to which it is linked, a 1,4-dialkyl-2-azabicyclo[2.2.2]octane structure, as well as the compounds of formulae (III), (IV), (V), (VII) and (VIII), are new and form part of the invention in the same way as the compounds of formula (I), for which they constitute the synthesis intermediates.

The compounds of formula (I) possess very advantageous pharmacological properties. These effects, while of the same nature as those of TRH, are exerted with markedly greater intensity. This is confirmed by their interaction with TRH-ergic receptors, observed in quantified autoradiography.

On the one hand, with respect to the central cholinergic system, the compounds of the invention are capable of restoring neuronal capacities for high-affinity choline uptake when this uptake, which is the limiting factor in acetyl choline synthesis, is experimentally depressed by barbiturate narcosis.

On the other hand, with respect to the central noradrenergic system, they are capable of counteracting the sedative and hypotensive action of an $\alpha_2$ agonist, clonidine, during acute ischaemia.

Thus, they jointly facilitate cholinergic neurotransmission involved in memory and alertness and noradrenergic neurotransmission involved in attention and motivation.

These properties have the advantage of being maintained after oral administration, which makes the compounds of the invention much more suitable for therapeutic use.

In particular, this latter feature, together with a high level of activity, makes the compounds of the present invention usable in the treatment of neurobehavioural disorders associated with normal or pathological aging and with acute or chronic degenerative diseases of the central nervous system, such as Alzheimer's disease, disorders of awareness and language, schizophrenia, depression, senile dementia, spinal trauma, amyotrophic lateral sclerosis or cerebrovascular accident.

The subject of the present invention is also pharmaceutical compositions containing, as active principle, at least one compound of general formula (I) or one of its addition salts with a pharmacologically acceptable acid, alone or in combination with one or more non-toxic, inert vehicles or excipients.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, sublingual preparations, pills, suppositories, creams, ointments, skin gels, and the like.

The appropriate dosage varies according to the patient's age and weight, the nature and severity of the condition and also the administration route. The latter can be oral, nasal, rectal or parenteral. Generally speaking, the unit dosage ranges between 0.05 and 300 mg for a treatment taken in 1 to 3 doses per 24 hours.

The examples which follow illustrate the invention and in no way limit the latter.

The abbreviations used in the examples are as follows:

PyroGlu in place of the 2-oxopyrrolidine-5-carbonyl radical, (N$^\tau$-Me)His in place of 1-methylhistidyl, the structural formula of which is as follows:

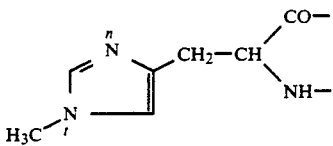

(N$^\pi$-Me)His in place of 3-methylhistidyl, the structural formula of which is as follows:

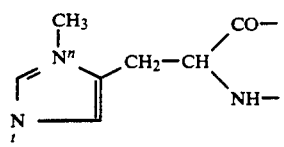

ABH in place of 2-azabicyclo[2.2.1]heptane-3-carbonyl,
tBOC in place of tert-butoxycarbonyl,
Z in place of benzyloxycarbonyl,
Leu in place of leucyl,
HomoPyroGlu in place of 2-oxopiperidine-6-carbonyl,
His in place of histidyl,
OTh in place of 2-oxothiazolidine-4-carbonyl,
dOPyr in place of 2,6-dioxo-1,2,3,6-tetrahydropyrimidine-4-carbonyl,
OAz in place of 2-oxoazetidine-4-carbonyl,
OiQ in place of 1-oxo-1,2,3,4-tetrahydroisoquinoline-3-carbonyl,
MIABO in place of 4-methyl-1-isopropyl-2-azabicyclo[2.2.2]octane-3-carbonyl,
dMABO in place of 1,4-dimethyl-2-azabicyclo[2.2.2]octane-3-carbonyl.

The preparations described below do not enable the products of the invention to be obtained. On the other hand, they lead to the production of intermediates useful in the synthesis of the products of the invention.

PREPARATION A: MIABO-OH "αβisomers"

STAGE A:
5-ISOPROPYL-8-METHYL-5,8-ETHANO-2-(4-CHLOROPHENYL)-1,3,5,8,8a-PENTAHYDRO-1,3-DIOXO-2H-IMIDAZO[1,5-a]PYRIDINE 43 g (0.18 mole) of 3-p-chlorophenyl-5-methoxyhydantoin (prepared according to D. BENI-, SHAI and E. GOLDSTEIN, TETRAHEDRON, 1971, 27, 3119–3127) are added to a solution of 98 g (0.72 mole) of 1-methyl-4-isopropyl-1,3-cyclohexadiene in 220 ml of anhydrous toluene. This mixture is brought to 160°–170° C. in an autoclave for 3 days.
The precipitate formed is drained and then recrystallized in isopropyl ether.
Yield: 35%
Melting point: 120° C.

| Elemental microanalysis: | | | | |
|---|---|---|---|---|
| | C % | H % | N % | Cl % |
| Calculated | 66.18 | 6.14 | 8.12 | 10.28 |
| Found | 65.93 | 6.02 | 8.11 | 10.22 |

STAGE B:
1-ISOPROPYL-4-METHYL-3-CARBOXY-2-AZABICYCLO[2.2.2]OCT-5-ENE 6.9 g (0.02 mole) of the compound prepared in stage A are hydrolysed by heating to reflux in 60 ml of 4N sodium hydroxide. After acidification with 6N HCl, the compound is bound to an ion exchange resin and then eluted with a 1N ammoniacal solution.
The expected product is obtained after concentration of the solvents.
Yield: 69%

STAGE C:
4-METHYL-1-ISOPROPYL-2-AZABICYCLO-[2.2.2]OCTANE-3-CARBOXYLIC ACID (MIABO-OH)

10 g (0.047 mole) of the compound prepared in stage B are hydrogenated in 165 ml of an ethanolic solution containing palladinized charcoal (10% palladium) at atmospheric pressure.
The expected product is then obtained in the form of two isomers arbitrarily designated α and β, with a 96% yield.

PREPARATION b: dMABO-OH "αβisomers"

STAGE A:
5,8-DIMETHYL-5,8-ETHANO-2-(4-CHLOROPHENYL)-1,3,5,8,8a-PENTAHYDRO-1,3-DIOXO-2H-IMIDAZO[1,5-a]PYRIDINE

Using the procedure described in stage A of Preparation A, but replacing 1-methyl-4-isopropyl-1,3-cyclohexadiene by 1,4-dimethyl-1,3-cyclohexadiene (prepared according to W. BRADY and S. J. NORTON, Synthesis, 1985, 704–705), the expected product is obtained.
Yield: 56%
Melting point: 178° C.

| Elemental microanalysis: | | | | |
|---|---|---|---|---|
| | C % | H % | N % | Cl % |
| Calculated | 64.46 | 5.41 | 8.84 | 11.19 |
| Found | 64.56 | 5.42 | 8.64 | 10.99 |

STAGE B:
1,4-DIMETHYL-3-CARBOXY-2-AZABICYCLO-[2.2.2]OCT-5-ENE

Using the procedure described in stage B of Preparation A, the expected product is obtained.
Yield: 60%

| Elemental microanalysis: | | | |
|---|---|---|---|
| | C % | H % | N % |
| Calculated | 66.27 | 8.34 | 7.73 |
| Found | 66.22 | 7.98 | 7.89 |

STAGE C:
1,4-DIMETHYL-2-AZA-BICYCLO[2.2.2]-OCTANE-3-CARBOXYLIC ACID (dMABO-OH)

Using the procedure described in stage C of Preparation A, the expected product is obtained in the form of two isomers arbitrarily designated α and β, with an 80% yield.

EXAMPLE 1:
(S)PyroGlu-(S)(N$^\tau$-Me)His-(1S,3S,4R)ABH-NH$_2$

STAGE A: tBOC-ABH-OH (mixture of four isomers)

The starting material used is 2-aza-3-carboxybicyclo-[2.2.1]heptane, abbreviated to ABH-OH, obtained according to the procedure described in Patent FR 2.525,604. This procedure enables the four isomers for which the ring junction is cis to be obtained simultaneously. 0.039 mole of ABH-OH (mixture of four isomers) is dissolved in a mixture containing 70 ml of dioxane and 30 ml of water, the mixture is cooled to 0° C., 39 ml of N sodium hydroxide are added and a solution of 0.039 mole of di-tert-butyl dicarbonate in 100 ml of dioxane is then added dropwise.

The mixture is left stirring for 30 minutes at a temperature between 0° and 5° C. and then for 2 hours at room temperature. The solvents are evaporated off under reduced pressure.

The residue is taken up with water, the mixture is acidified with citric acid to pH 4 and the aqueous phase is extracted with ethyl acetate. The organic phase is washed with 10% strength aqueous sodium chloride solution, dried over anhydrous calcium sulphate, filtered and concentrated under reduced pressure. The product is recrystallized in n-pentane.

Yield: 71%

Infrared (nujol):

$\nu$ CO (acid): 1740 cm$^{-1}$
$\nu$ CO (carbamate): 1640 cm$^{-1}$

| Elemental microanalysis: | | | |
|---|---|---|---|
| | C % | H % | N % |
| calculated | 59.73 | 7.94 | 5.80 |
| found | 59.56 | 7.72 | 5.80 |

STAGE B: tBOC-ABH-NH$_2$ (mixture of four isomers)

4.27 ml of triethylamine and then 2.97 ml of freshly distilled ethyl chloroformate dissolved in 20 ml of tetrahydrofuran are added to a solution, cooled in an ice/salt mixture (temperature: $-10°$ C.), of 6.7 g (0.028 mole) of tBOC-ABH-OH, obtained in stage A, in 80 ml of tetrahydrofuran. A precipitate forms, which is left stirring for a quarter of an hour at $-10°$ C. 5.27 ml of concentrated ammonia solution are then added and the mixture is left stirring for 30 minutes at $-10°$ C. The mixture is allowed to return to room temperature. After evaporation of the solvents under reduced pressure, the residue is taken up with aqueous citric acid solution, pH 4.

The acidic aqueous phase is extracted with ethyl acetate. The organic phase is then washed with aqueous sodium bicarbonate solution and thereafter with water, and finally dried over anhydrous calcium sulphate. It is filtered and concentrated under reduced pressure.

Yield: 90%

Proton nuclear magnetic resonance (CDCl$_3$):

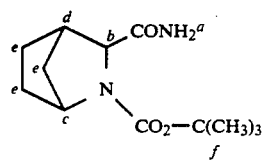

$^a\delta$ between 6.2 and 5.7 ppm (2H, m)
$^b\delta$ = 4.5 ppm (1H, m)
$^c\delta$ = 4.1 ppm (1H, m)
$^d\delta$ = 2.9 ppm (1H, m)
$^e\delta$ = 1.6 ppm (6H, m)
$^f\delta$ = 1.4 ppm (9H, s)

STAGE C: ABH-NH$_2$. HCl (mixture of four isomers)

A solution of 87.5 g (0.365 mole) of tBOC-ABH-NH$_2$ in 1 liter of anhydrous dioxane is saturated with hydrogen chloride gas and the mixture is left stirring for 18 hours at room temperature.

The dioxane is evaporated off and the residue is taken up with 300 ml of anhydrous ether.

The product obtained is drained, washed and dried.

Yield: 86%

Proton nuclear magnetic resonance (CDCl$_3$):

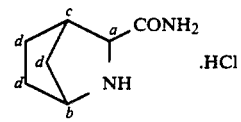

$^a\delta$ = 4.4 ppm (1H, m)
$^b\delta$ = 4.1 ppm (1H, m)
$^c\delta$ = 3.0 ppm (1H, m)
$^d\delta$ between 2 and 1.3 ppm (6H, m)

STAGE D: tBOC-(S)(N$^\tau$-Me)His-ABH-NH$_2$ (mixture of isomers)

Using the peptide coupling method (DCC/HOBT) described by W. KONIG and R. GEIGER (Ber, 103, 788, 1970) and dimethylformamide as a solvent, tBOC-(S)(N$^\tau$-Me)His-ABH-NH$_2$ is prepared from 0.0181 mole of ABH-NH$_2$, obtained in the preceding stage, and 0.0181 mole of tBOC-(S)(N$^\tau$-Me)His-OH.

Yield: 85%

The mixture of diastereoisomers obtained is separated by chromatography on a silica column, eluting with a dichloromethane/methanol/ammonia solution mixture in the proportions 9:1:0.1.

The Diels-Alder condensation used for the production of ABH-OH (Patent FR 2,525,604) implies that it is obtained with cis ring junctions, that is to say in the form of two pairs of enantiomers. Coupling with tBOC-(S)(N$^\tau$-Me)-His-OH hence gives rise to 4 diastereoisomers, which are separated under the conditions described previously and whose absolute configurations were determined with X-rays.

STAGE E: (S)(N$^\tau$-Me)His-(1S,3S,4R)ABH-NH$_2$ dihydrochloride

The isomer tBOC-(S)(N$^\tau$-Me)His-(1S,3S,4R)ABH-NH$_2$ is deprotected according to the method described in stage C.

Yield: 95%

This compound may also be obtained by replacing ABH-NH$_2$ (mixture of isomers) in stage D by the isomer (1S,3S,4R)ABH-NH$_2$ obtained in stage E of Example 5 (in this case, the separation of diastereoisomers described in the preceding stage is superfluous).

STAGE F: Z-(S)PyroGlu-(S)(N$^\tau$-Me)His-(1S,3S,4R)-ABH-NH$_2$

Using the peptide coupling method described by G. W. ANDERSON and J. E. ZIMMERMAN (JACS, 85, 3039, 1963), 0.033 mole of (S)($N^\tau$-Me)His-(1S,3S,4R)ABH-NH$_2$, obtained in the preceding stage, is reacted with 0.033 mole of the activated N-hydroxysuccinimide ester of Z-(S)PyroGlu-OH in 100 ml of dimethylformamide and 0.066 mole of triethylamine.

After the usual treatment and chromatography on a silica column using an acetone/water mixture in the proportions 95:5 as eluant, the expected product is obtained.

Yield: 57%

STAGE G:
(S)PyroGlu-(S)($N^\tau$-Me)His-(1S,3S,4R)-ABH-NH$_2$

The product obtained in the preceding stage is deprotected by catalytic hydrogenation in ethanol in the presence of palladium on charcoal used as a catalyst.

After filtration of the catalyst and evaporation of the solvent, the product is chromatographed on silica, using a dichloromethane/methanol/ammonia solution mixture in the proportions 80:20:1 as eluant.

Elemental microanalysis:

|            | C %   | H %  | N %   |
|------------|-------|------|-------|
| calculated | 56.70 | 6.51 | 20.88 |
| found      | 56.35 | 6.08 | 20.80 |

Proton nuclear magnetic resonance (D$_2$O):

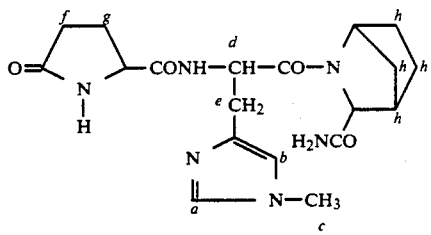

$^a\delta = 7.6$ ppm (1H, s)
$^b\delta = 7.0$ ppm (1H, s)
$^c\delta = 3.7$ ppm (3H, s)
$^d\delta = 5$ ppm (1H, t)
$^e\delta = 3.1$ ppm (2H, d)
$^{f+g}\delta$ between 2.3 and 2.9 ppm (4H, m)
$^h\delta$ between 1.1 and 2.1 (7H, m)

EXAMPLE 2:
(S)PyroGlu-(S)($N^\tau$-Me)His-(1R,3S,4S)-ABH-NH$_2$

Using the procedure described in Example 1, but replacing the isomer tBOC-(S)($N^\tau$-Me)His-(1S,3S,4R)ABH-NH$_2$ in stage E by the isomer tBOC-(S)($N^\tau$-Me)His(1R,3S,4S)-ABH-N H$_2$ obtained in stage D, the expected product is obtained.

Proton nuclear magnetic resonance (D$_2$O):

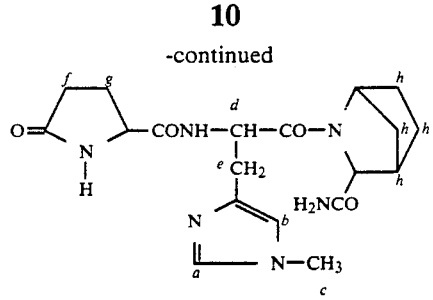

$^a\delta = 8.0$ ppm (1H, s)
$^b\delta = 7.3$ ppm (1H, s)
$^c\delta = 3.9$ ppm (3H, s)
$^e\delta = 3.3$ ppm (2H, d)
$^d\delta = $ between 4.2 and 5.3 ppm (1H, m)
$^{f+g}\delta$ between 2.5 and 3.7 ppm (4H, m)
$^h\delta$ between 1.4 and 2.3 ppm (7H, m)

EXAMPLE 3:
(S)PyroGlu-(S)($N^\tau$-Me)His-(1S,3R,4R)-ABH-NH$_2$

Using the procedure described in Example 1, but replacing the isomer tBOC-(S)($N^\tau$-Me)His-(1S,3S,4R)ABH-NH$_2$ in stage E by the isomer tBOC(S)($N^\tau$-Me)His-(1S,3S,4R)-ABH-NH$_2$ obtained in stage D, the expected product is obtained.

Proton nuclear magnetic resonance (D$_2$O):

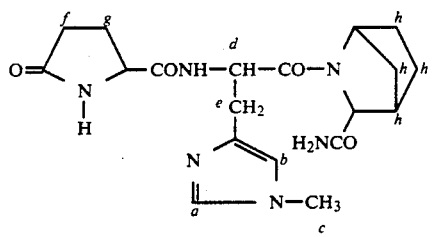

$^a\delta = 7.6$ ppm (1H, s)
$^b\delta = 6.9$ ppm (1H, s)
$^c\delta = 3.7$ ppm (3H, s)
$^d\delta = 4.9$ ppm (1H, m)
$^e\delta = 3.0$ ppm (2H, m)
$^{f+g}\delta$ between 2.3 and 2.8 ppm (4H, m)
$^h\delta$ between 1.3 and 2.1 ppm (7H, m)

EXAMPLE 4:
(S)PyroGlu-(S)($N^\tau$-Me)His-(1R,3R,4S)ABH-NH$_2$

Using the procedure described in Example 1, but replacing the isomer tBOC-(S)($N^\tau$-Me)His-(1S,3S,4R)ABH-NH$_2$ in stage E by the isomer tBOC-(S)($N^\tau$-Me)His-(1R,3R,4S)ABH-NH$_2$ obtained in stage D, the expected product is obtained.

Proton nuclear magnetic resonance (D$_2$O):

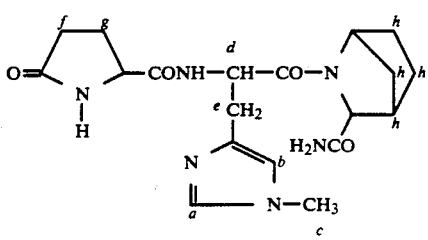

$^a\delta$ = 7.7 ppm (1H, s)
$^b\delta$ = 7.0 ppm (1H, s)
$^c\delta$ = 3.7 ppm (3H, s)
$^e\delta$ = 3.0 ppm (2H, d)
$^d\delta$ = between 4.1 and 5 ppm (1H, m)
$^{f+g}\delta$ between 2.3 and 2.9 ppm (4H, m)
$^h\delta$ between 1.5 and 2.2 ppm (7H, m)

EXAMPLE 5:
(S)PyroGlu-(S)Leu-(1S,3S,4R)ABH-NH₂

STAGE A: ABH-OH [mixture of (1S,3S,4R) and (1R,3R,4S) isomers]

100 g of the racemic mixture of the four isomers of ABH-OH, obtained according to the method described in Patent FR 2,525,604, are dissolved in the heated state in 1,400 cm³ of anhydrous methanol. This solution is allowed to cool slowly and with stirring for 20 hours. The precipitate formed is then filtered and rinsed with 50 cm³ of anhydrous methanol, then dried; 31.5 g of ABH-OH [mixture of (1S,3S,4R) and (1R,3R,4S) isomers] are thereby obtained. The filtrate is then taken to dryness; the residue obtained is recrystallized in anhydrous ethanol and then in anhydrous methanol, and leads to a further 15 g of expected product.
The purity of this mixture of isomers is monitored by liquid chromatography under the following conditions:
Column:
length: 25 cm
internal diameter: 4.5 mm
Stationary phase: Ultra Base (particle size: 5 μm)
Mobile phase: aqueous phase containing
1.25% of trifluoro-acetic acid: 200 volumes
acetonitrile: 5 volumes
Flow rate: 1 ml/min
Temperature: 20° C.
Retention time:
ABH-OH [mixture of (1S,3S,4R) and (1R,3R,4S) isomers]* : 5.5 min
ABH-OH [mixture of (1R,3S,4S) and (1S,3R,4R) isomers]*: 6.1 min
* Definition: The first mixture of isomers (retention time 5.5 minutes) thereby obtained, when used as the starting material in stage A of Example 1 (instead of the mixture of the four isomers obtained according to Patent FR 2,525,604) makes it possible, working according to the protocols described in stages A, B, C and D of Example 1, to obtain the two single isomers (1S,3S,4R) and (1R,3R,4S) of tBOC(S)(N$^\tau$-Me)His-ABH-NH₂.
Similarly, if the mixture of 2 isomers having a retention time of 6.1 minutes is used as the starting material in stage A of Example 1, the (1R,3S,4S) and (1S,3R,4R) isomers of tBOC(S)(N$^\tau$-Me)His-ABH-NH₂ are obtained in stage D of Example 1.

STAGE B: tBOC-ABH-OH [mixture of (1S,3S,4R) and (1R,3R,4S) isomers]

Using the procedure described in stage A of Example 1, the expected product, is obtained.
Yield: 91%
Infrared (nujol):
νCO (acid): 1740 cm⁻¹
νCO (carbamate): 1640 cm⁻¹

STAGE C: tBOC-ABH-NH₂ [mixture of (1S,3S,4R) and (1R,3R,4S) isomers]

Using the procedure described in stage B of Example 1, the expected product is obtained.
Yield: 97%

Proton nuclear magnetic resonance (CDCl₃):

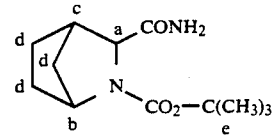

a δ = 4.5 ppm (1H, m)
b δ = 4.1 ppm (1H, m)
c δ = 2.9 ppm (1H, m)
d δ = 1.6 ppm (6H, m)
e δ = 1.4 ppm (9H, s)

STAGE D: ABH-NH₂. HCl [mixture of (1S,3S,4R) and (1R,3R,4S) isomers]

Using the procedure described in stage C of Example 1, the expected product is obtained.
Yield: 86%

| Elemental microanalysis: | | | | |
|---|---|---|---|---|
| | C % | H % | N % | Cl % |
| Calculated | 47.60 | 7.42 | 15.86 | 20.07 |
| Found | 47.90 | 7.40 | 15.83 | 19.82 |

STAGE E: (1S,3S,4R)ABH-NH₂

25.5 g (0.155 mole) of ABH-NH₂.HCl [mixture of (1S,3S,4R) and (1R,3R,4S) isomers] obtained in the preceding stage are dissolved in 250 cm³ of water. This solution is neutralized with 10N sodium hydroxide and taken to dryness. The residue stirred in 200 cm³ of anhydrous isopropanol is filtered. The filtrate is then evaporated, the residue is taken up with 250 cm³ of methylene chloride and the mixture is filtered to remove traces of sodium chloride and then evaporated to dryness. After dissolution in 400 cm³ of anhydrous methanol, 20.8 g (0.139 mole) of D(−)-tartaric acid are added to this solution and the mixture is then brought to reflux with stirring until dissolution is complete. The mixture is cooled slowly and with stirring for 18 hours. The precipitate formed is filtered off and rinsed with 25 cm³ of methanol.
This purification operation will be repeated until an optically pure isomer is obtained. The enantiomeric purity is monitored by liquid chromatography under the following conditions after derivatization with MOSHER's reagent.
Column:
length: 15 cm
internal diameter: 6.0 mm
Stationary phase: ASAHI PAK ODP-50 (particle size: 5 μm)
Mobile phase:
acetonitrile: 65 volumes
water: 35 volumes
H₂SO₄: 0.5 volume
Flow rate: 1 ml/min Retention time:
(1S,3S,4R)ABH-NH$_2$: 6.4 min
(1R,3R,4S)ABH-NH$_2$: 6.8 min The (1S,3S,4R)ABH-NH$_2$ tartrate is then dissolved in water, bound to an ion exchange resin and thereafter eluted with a 10% strength ammoniacal solution. After evaporation, the expected product is obtained.
Yield: 60%

STAGE F: tBOC-(S)Leu-(1S,3S,4R)ABH-NH$_2$

Using the procedure described in stage D of Example 1, but replacing tBOC-(S)(N$^T$-Me)His-OH by tBOC-(S)Leu-OH, the expected product is obtained.

STAGE G: (S)Leu-(1S,3S,4R)ABH-NH$_2$ hydrochloride

Using the procedure as described in stage E of Example 1, the expected product is obtained.
Yield: 87%

STAGE H: Z-(S)PyroGlu-(S)Leu-(1S,3S,4R)ABH-NH$_2$

Using the procedure described in stage F of Example 1, but replacing (S)(N$^T$-Me)His-(1S,3S,4R)ABH-NH$_2$ by (S)Leu-(1S,3S,4R)ABH-NH$_2$ obtained in the preceding stage, the expected product is obtained.
Yield: 72%

STAGE I: (S)PyroGlu-(S)Leu-(1S,3S,4R)ABH-NH$_2$

Using the procedure described in stage G of Example 1, but replacing Z-(S)-PyroGlu-(S)(N$^\tau$-Me)His-(1S,3S,4R)ABH-NH$_2$ by Z-(S)PyroGlu-(S)Leu-(1S,3S,4R)ABH-NH$_2$ obtained in the preceding stage, the expected product is obtained.
Yield: 57%

| Elemental microanalysis: | | | |
|---|---|---|---|
|  | C % | H % | N % |
| Calculated | 59.32 | 7.74 | 15.37 |
| Found | 59.11 | 7.93 | 15.66 |

EXAMPLE 6: (S)PyroGlu-(S)(N$^\pi$-Me)His-(1S,3S,4R)-ABH-NH$_2$

Stages A to E are identical to stages A to E of Example 5.

STAGE F: tBOC-(S)(N$^\pi$-Me)His-(1S,3S,4R)ABH-NH$_2$

Using the procedure described in stage F of Example 5, but replacing tBOC-(S)Leu-OH by tBOC-(S)-(N$^\pi$-Me)His-OH, the expected product is obtained.
Yield: 83%

STAGE G: (S)(N$^\pi$-Me)His-(1S,3S,4R)ABH-NH$_2$ dihydrochloride

Using the procedure described in stage G of Example 5, but replacing tBOC-(S)Leu-(1S,3S,4R)ABH-NH$_2$ by tBOC-(S)(N$^\pi$-Me)His-(1S,3S,4R)ABH-NH$_2$ obtained in the preceding stage, the expected product is obtained.
Yield: 81%

STAGE H: Z-(S)pyroGlu-(S)(N$^\pi$-Me)His-(1S,3S,4R)-ABH-NH$_2$

Using the procedure described in stage H of Example 5, but replacing (S)Leu-(1S,3S,4R)ABH-NH$_2$ by (S)(N$^\pi$-Me)His-(1S,3S,4R)ABH-NH$_2$ dihydrochloride obtained in the preceding stage, the expected product is obtained.

STAGE I: (S)PyroGlu-(S)(N$^\pi$-Me)His-(1S,3S,4R)-ABH-NH$_2$

Using the procedure described in stage I of Example 5, but replacing Z-(S)PyroGlu-(S)Leu-(1S,3S,4R)-ABH-NH$_2$ by Z-(S)PyroGlu-(S)(N$^\pi$-Me)His-(1S,3S,4R)ABH-NH$_2$ obtained in the preceding stage, the expected product is obtained.
Yield: 66%

Proton nuclear magnetic resonance (D$_2$O):

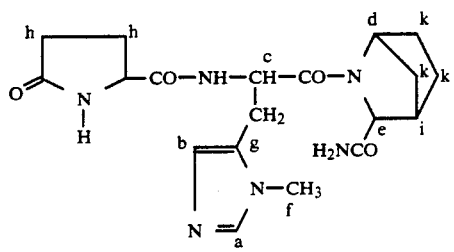

a δ = 7.5 ppm (1H, s)
b δ = 6.8 ppm (1H, s)
c δ = 5.0 ppm (1H, m)
d δ = 4.5 ppm (1H, m)
e δ = 4.3 ppm (1H, m)
f δ = 3.6 ppm (3H, s)
g δ = 3.0 ppm (2H, m)
h δ = 2.5 ppm (4H, m)
i δ = 2.7 ppm (1H, m)
k δ = 1.6 ppm (6H, m)

EXAMPLE 7: (S)HomoPyroGlu-(S)(N$^\pi$-Me)His-(1S,3S,4R)ABH-NH$_2$

Stages A to G are identical to stages A to G of Example 6.

STAGE H: (S)HomoPyroGlu-(S)(N$^\pi$-Me)His-(1S,3S,4R)ABH-NH$_2$

Using the procedure described in stage H of Example 6, but replacing the activated N-hydroxysuccinimide ester of Z-(S)PyroGlu-OH by the activated hydroxysuccinimide ester of (S)HomoPyroGlu-OH, the expected product is obtained.
Yield: 83%

| Elemental microanalysis: | | | |
|---|---|---|---|
|  | C % | H % | N % |
| Calculated | 57.68 | 6.78 | 20.18 |
| Found | 57.60 | 6.75 | 19.88 |

EXAMPLE 8: (S)HomoPyroGlu-(S)Leu-(1S,3S,4R)-ABH-NH$_2$

Stages A to G are identical to stages A to G of Example 5.

STAGE H: (S)HomoPyroGlu-(S)Leu-(1S,3S,4R)-ABH-NH$_2$

Using the procedure described in stage H of Example 5, but replacing the activated hydroxysuccinimide ester of Z-(S)PyroGlu-OH by the activated N-hydroxysuccinimide ester of (S)HomoPyroGlu-OH, the expected product is obtained.

Yield: 64%

Proton nuclear magnetic resonance (DMSO-d6):

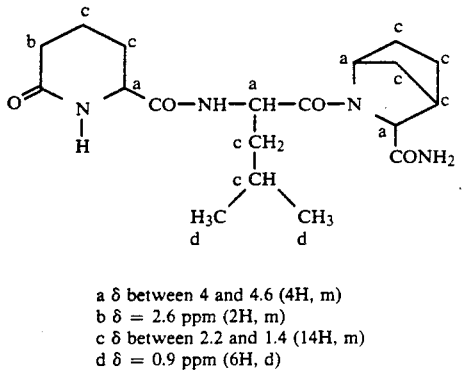

a δ between 4 and 4.6 (4H, m)
b δ = 2.6 ppm (2H, m)
c δ between 2.2 and 1.4 (14H, m)
d δ = 0.9 ppm (6H, d)

EXAMPLE 9:
(S)PyroGlu-(S)His-(1S,3S,4R)ABH-NH2

Using the procedure described in Example 5, but replacing tBOC-(S)Leu-OH in stage F by tBOC-(S)His-OH, the expected product is obtained.

Proton nuclear magnetic resonance (DMSO-d6):

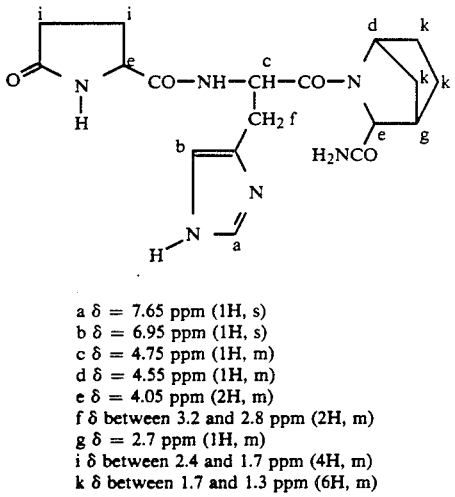

a δ = 7.65 ppm (1H, s)
b δ = 6.95 ppm (1H, s)
c δ = 4.75 ppm (1H, m)
d δ = 4.55 ppm (1H, m)
e δ = 4.05 ppm (2H, m)
f δ between 3.2 and 2.8 ppm (2H, m)
g δ = 2.7 ppm (1H, m)
i δ between 2.4 and 1.7 ppm (4H, m)
k δ between 1.7 and 1.3 ppm (6H, m)

EXAMPLE 10:
(S)HomoPyroGlu-(S)His-(1S,3S,4R)-ABH-NH2

Using the procedure described in Example 9, but replacing Z-(S)PyroGlu-OH in stage H by (S)HomoPyroGlu-OH, the expected product is obtained.

Proton nuclear magnetic resonance (DMSO-d6):

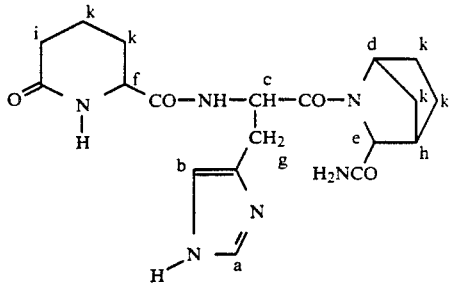

a δ = 7.7 ppm (1H, s)
b δ = 6.95 ppm (1H, s)
c δ = 4.75 ppm (1H, m)
d δ = 4.55 ppm (1H, m)
e δ = 4.00 ppm (1H, d)
f δ = 3.90 ppm (1H, m)
g δ between 3.1 and 2.8 ppm (2H, m)
h δ = 2.75 ppm (1H, m)
i δ = 2.1 ppm (2H, t)
k δ between 2.0 and 1.2 ppm (10H, m)

EXAMPLE 11:
(S)HomoPyroGlu-(S)(Nτ-Me(His-(1S,3S,4R)ABH-NH2

Using the procedure described in Example 7, but replacing tBOC-(S)(Nπ-Me)His-OH in stage F by tBOC-(S)(Nτ-Me)His-OH, the expected product is obtained.

Proton nuclear magnetic resonance (CDCl3):

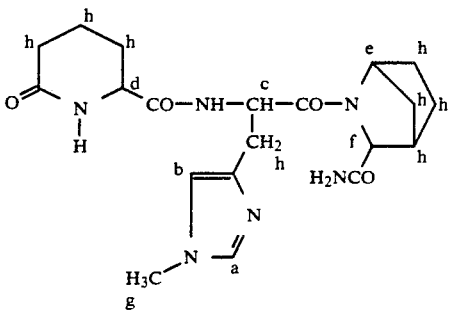

a δ = 7.3 ppm (1H, s)
b δ = 6.7 ppm (1H, s)
c δ = 4.9 ppm (1H, m)
d δ = 4.5 ppm (1H, m)
e δ = 4.3 ppm (1H, m)
f δ = 4.0 ppm (1H, m)
g δ = 3.6 ppm (3H, s)
h between 3.3 and 1.5 ppm (15H, m)

EXAMPLE 12:
(S)PyroGlu-(S)His-(1R,3R,4S)ABH-NH2

Using the procedure described in Example 9, but replacing (1S,3S,4R)ABH-NH2 in stage F by (1R,3R,4S)ABH-NH2 obtained in the preceding stage, the expected product is obtained.

EXAMPLE 13:
OTh-(S)(Nτ-Me)His-(1S,3S,4R)ABH-NH2

Using the procedure described in Example 5, but replacing tBOC-(S)Leu-OH in stage F by tBOC-(S)(Nτ-Me)His-OH, and Z-(S)PyroGlu-OH in stage H by Z-OTh-OH, the expected product is obtained.

Yield: 66%

| Elemental microanalysis: | | | | |
| --- | --- | --- | --- | --- |
| | C % | H % | N % | S % |
| Calculated | 51.42 | 5.75 | 19.99 | 7.63 |
| Found | 51.33 | 5.76 | 20.09 | 7.98 |

EXAMPLE 14:
dOPyr-(S)(N$^\tau$-Me)His-(1S,3S,4)ABH-NH$_2$

Using the procedure described in Example 13, but replacing Z-OTh-OH in stage H by Z-dOPyr-OH, the expected product is obtained.
Yield: 53%

Proton nuclear magnetic resonance (DMSO-d$_6$):

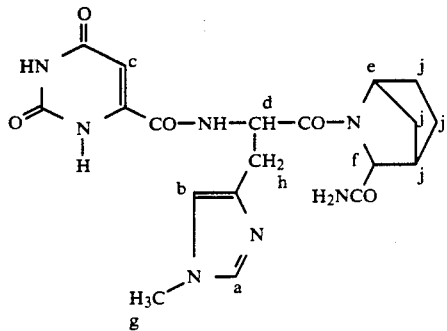

a δ = 7.4 ppm (1H, s)
b δ = 6.9 ppm (1H, s)
c δ = 6.0 ppm (1H, s)
d δ = 4.8 ppm (1H, m)
e δ = 4.6 ppm (1H, m)
f δ = 4.0 ppm (1H, d)
g δ = 3.6 ppm (3H, s)
h δ = 2.9 ppm (2H, m)
i δ = 2.7 ppm (1H, m)
j δ = 1.5 ppm (6H, m)

EXAMPLE 15: OAz-(S)Leu-(1S,3S,4R)ABH-NH$_2$

Using the procedure described in Example 5, but replacing Z-(S)PyroGlu-OH in stage H by Z-OAz-OH prepared according to K. TANAKA, S. YOSHIFUZI and Y. NITTA, Heterocycles, 1986, 24, (9), 2539, the expected product is obtained.
Yield: 43%

Proton nuclear magnetic resonance (DMSO-d$_6$):

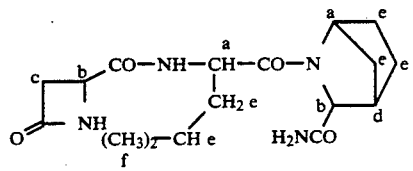

a δ = 4.5 ppm (2H, m)
b δ = 4.0 ppm (2H, m)
c = between 3.1 and 2.6 ppm (2H, m)
d δ = 2.7 ppm (1H, m)
e δ = 1.6 ppm (9H, m)
f δ = 0.9 ppm (6H, m)

EXAMPLE 16: OiQ-(S)Leu-(1S,3S,4R)ABH-NH$_2$

Using the procedure described in Example 5, but replacing Z-(S)PyroGlu-OH in stage H by Z-OiQ-OH prepared according to H. MAEDA and M. SUZUKI, Chem. Pharm. Bull. 1988, 36(1), 190, the expected product is obtained.

EXAMPLE 17:
(S)HomoPyroGlu-(S)Leu-MIABO-NH$_2$ "α isomar"

Using the procedure described in Example 8, but replacing ABH-OH "αδ isomers" in stage A by MIABO-OH "αβ isomers" obtained in Preparation A, the expected product is obtained.

EXAMPLE 18:
(S)PyroGlu-(S)(N$^\tau$-Me)His-dMABO-NH$_2$ "α isomer"

Using the procedure described in Example 6, but replacing ABH-OH "αδ isomers" in stage A by dMABO-OH "αβ isomers" obtained in Preparation B, the expected product is obtained.

EXAMPLE 19: (S)PyroGlu-(S)Leu-dMABO-NH$_2$ "α isomer"

Using the procedure described in Example 5, but replacing ABH-OH "αδ isomers" in stage A by dMABO-OH "αβ isomers" obtained in Preparation B, the expected product is obtained.
Yield: 53%

| Elemental microanalysis: | | | |
| --- | --- | --- | --- |
| | C % | H % | N % |
| Calculated | 62.05 | 8.43 | 13.78 |
| Found | 62.20 | 8.66 | 13.33 |

EXAMPLE 20: (S)PyroGlu-(S)Leu-MIABO-NH$_2$ "α isomer"

Using the procedure described in Example 5, but replacing ABH-OH "αδ isomers" in stage A by MIABO-OH "αβ isomers" obtained in Preparation A, the expected product is obtained.

EXAMPLE 21:
OiQ-(S)(N$^\tau$-Me)His-(1S,3S,4R)ABH-NH$_2$

Using the procedure described in Example 5, but replacing tBOC-(S)Leu-OH in stage F by tBOC-(S)(N$^\tau$-Me)His-OH, and Z-(S)PyroGlu-OH in stage H by Z-OiQ-OH prepared according to M. MAEDA and M. SUZUKI, Chem. Pharm. Bull. 1988, 36 (1), 190, the expected product is obtained.

| Elemental microanalysis: | | | |
| --- | --- | --- | --- |
| | C % | H % | N % |
| Calculated | 62.06 | 6.08 | 18.09 |
| Found | 61.71 | 6.55 | 18.44 |

EXAMPLE 22:
(S)OAz-(S)(N$^\tau$-Me)His-(1S,3S,4R)ABH-NH$_2$

Using the procedure described in Example 5, but replacing tBOC-(S)Leu-OH in stage F by tBOC-(S)(N$^\tau$-Me)His-OH, and Z-(S)PyroGlu-OH in stage H by Z-OAz-OH prepared according to K. TANAKA, S. YOSHIFUZI and Y. NITTA, Heterocycles, 1986, 24 (9), 2539, the expected product is obtained.
Yield: 51%

| Elemental microanalysis: | | | |
|---|---|---|---|
| | C % | H % | N % |
| Calculated | 55.66 | 6.23 | 21.64 |
| Found | 56.03 | 6.51 | 21.61 |

EXAMPLE 23: (S)OAz-(S)His-(1S,3S,4R)ABH-NH$_2$

Using the procedure described in Example 5, but replacing tBOC-(S)Leu-OH in stage F by tBOC-(S)His-OH, and Z-(S)PyroGlu-OH in stage H by Z-OAz-OH prepared according to K. TANAKA, S. YOSHIFUZI and Y. NITTA, Heterocycles, 1986, 24 (9), 2539, the expected product is obtained.

Yield: 61%

Proton nuclear magnetic resonance (DMSO-d$_6$)

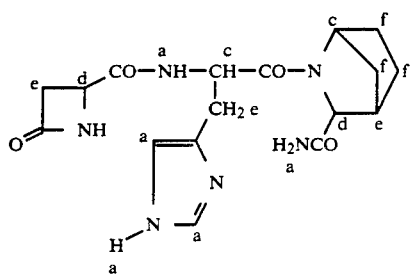

a δ between 8.2 and 7.0 ppm (6H, m)
b δ = 4.8 ppm (1H, m)
c δ = 4.6 ppm (1H, m)
d δ = 4.0 ppm (2H, m)
e δ = between 3.1 and 2.5 ppm (5H, m)
f δ ≃ 1.5 ppm (6H, m)

PHARMACOLOGICAL STUDY OF THE DERIVATIVES OF THE INVENTION

EXAMPLE 24: Barbiturate-induced cholinergic deficit in rats

In rats, narcosis induced by pentobarbital (60 mg/kg ip) brings about markedly reduced functioning of cholinergic neurotransmission, which is manifested, in particular, in the fall (−48%) in synaptosomal high-affinity choline uptake (HACU) measured after 20 minutes of narcosis. This sodium-dependent uptake normally constitutes the limiting factor in acetyl choline synthesis. Administration of TRH (10 mg/kg ip) simultaneously with that of pentobarbital does not inhibit the narcosis, but counteracts (−35%) the fall in HACU induced by the barbiturate.

Under the same conditions and at a dose of 10 mg/kg ip, the compound of Example 1 inhibits by 66% the fall in HACU.

EXAMPLE 25: Oxotremorine-induced tremor in mice

Administration of oxotremorine (0.5 mg/kg ip) in mice leads to muscarinic neurological symptoms of central origin, of which tremor is the most marked expression. This reaches its maximum intensity after 15 minutes and disappears in one hour. Administration of TRH (10 mg/kg ip) 30 minutes before oxotremorine leads to a boosting (+90%) of the tremor, measured at the peak of action of the muscarine agonist. However, this effect is no longer apparent at a dose of 3 mg/kg ip.

Under the same conditions, the compound of Example 1 exerts the same boosting effect (+90%) at a dose of 10 mg/kg ip, without itself inducing tremor.

This effect is still marked (+60%) and significant at a dose of 3 mg/kg ip. It is still manifested 60 minutes after the administration of oxotremorine, whereas control animals no longer exhibit tremor.

Administered orally at a dose of 10 mg/kg, the compound of Example 1 exerts an effect identical to that observed when administered ip at a dose of 3 mg/kg. TRH administered orally exerts no boosting effect.

The origin of this boosting effect on the central actions of oxotremorine appears to differ under our experimental conditions between TRH and the compound taken as an example. In effect, in the presence of a very low dose (0.01 mg/kg) of scopolamine, which does not counteract the tremor in control animals, the boosting effect of the compound of Example 1 disappears whereas that of TRH persists.

The compound of Example 1 hence appears to be a cholinergic facilitating agent, while TRH might exert this boosting effect through dopaminergic agonism.

EXAMPLE 26: Interaction with clonidine

In mice, clonidine, a central α$_2$ agonist, brings about a cerebral hypometabolizing sedative effect which leads to an increase (+60%) in the cerebral survival time on sudden cardiac arrest caused by the intravenous injection of a massive dose of MgCl$_2$.

When administered simultaneously with clonidine, TRH antagonizes the effect of the α$_2$ agonist (1 mg/kg ip: −20%; 3 mg/kg ip: −80%) without having an effect on its own in the test used.

Under the same conditions, the compound of Example 1 antagonizes the sedative effect of clonidine (0.3 mg/kg ip: −20%; 1 mg/kg ip: −70%).

The compound of Example 1 hence facilitates noradrenergic neurotransmission, and counteracts the sedation caused by inhibition of this neurotransmission.

We claim:

1. A compound selected from those of the formula (I):

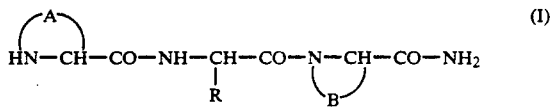

in which:
A represents, with the nitrogen and carbon atoms to which it is linked:
  a 2-oxo-5-pyrrolidinyl group,
  a 2-oxo-6-piperidyl group,
  a 2,6-dioxo-1,2,3,6-tetrahydro-4-pyrimidinyl group,
  a 2-oxo-4-thiazolidinyl group,
  a 2-oxo-4-azetidinyl group,
  a 1-oxo-1,2,3,4-tetrahydro-3-isoquinolyl group,
B represents, with the nitrogen and carbon atoms to which it is linked, a saturated polycyclic structure selected from 2-azabicyclo[2.2.1]heptane or 1,4-di(-linear or branched lower alkyl)-2-azabicyclo[2.2.2]-octane,
R represents a hydrogen atom, a linear or branched lower alkyl group or a (4-imidazolyl)methyl group optionally substituted on one of the nitrogen atoms with a linear or branched lower alkyl radical, the term lower indicating that the groups thus qualified contain from 1 to 6 carbon atoms, their enantiomers, diastereoisomers and epimers, as well as their addition salts with a pharmaceutically acceptable acid.

2. A compound according to claim 1, such that B, with the nitrogen and carbon atoms to which it is linked, forms a 2-azabicyclo[2.2.1]heptane ring-system, their enantiomers, diastereoisomers and epimers, as well as their addition salts with a pharmaceutically acceptable acid.

3. A compound according to claim 1, such that B, with the nitrogen and carbon atoms to which it is linked, forms a 1,4-dialkyl-2-azabicyclo[2.2.2]octane ring-system, their enantiomers, diastereoisomers and epimers, as well as their addition salts with a pharmaceutically acceptable acid.

4. A compound according to claim 1, such that B, with the nitrogen and carbon atoms to which it is linked, forms a 1,4-dimethyl-2-azabicyclo[2.2.2]octane ring-system, their enantiomers, diastereoisomers and epimers, as well as their addition salts with a pharmaceutically acceptable acid.

5. A compound according to claim 1, such that B, with the nitrogen and carbon atoms to which it is linked, forms a 4-methyl-1-isopropyl-2-azabicyclo[2.2.2]-octane ring-system, their enantiomers, diastereoisomers and epimers, as well as their addition salts with a pharmaceutically acceptable acid.

6. A compound according to claim 1, which is PyroGlu-($N^\tau$-Me)His-ABH-$NH_2$, its enantiomers, diastereoisomers and epimers, as well as its addition salts with a pharmaceutically acceptable acid, PyroGlu representing a 2-oxopyrrolidine-5-carbonyl radical, ($N^\tau$-Me)His representing a 1-methylhistidyl radical and ABH a 2-azabicyclo[2.2.1]heptane-3-carbonyl radical.

7. A compound according to claim 1, which is PyroGlu-Leu-ABH-$NH_2$, its diastereoisomers, enantiomers and epimers, as well as its addition salts with a pharmaceutically acceptable acid, PyroGlu representing a 2-oxopyrrolidine-5-carbonyl radical, Leu representing a leucyl radical and ABH a 2-azabicyclo[2.2.1]heptane-3-carbonyl radical.

8. A compound according to claim 1, which is PyroGlu-($N^\pi$-Me)His-ABH-$NH_2$, its diastereoisomers, enantiomers and epimers, as well as its addition salts with a pharmaceutically acceptable acid, PyroGlu representing a 2-oxopyrrolidine-5-carbonyl radical, ($N^\pi$-Me)His a 3-methylhistidyl radical and ABH a 2-azabicyclo[2.2.1]-heptane-3-carbonyl radical.

9. A compound according to claim 1, which is HomoPyroGlu-($N^\pi$-Me)His-ABH-$NH_2$, its diastereoisomers, enantiomers and epimers, as well as its addition salts with a pharmaceutically acceptable acid, HomoPyroGlu representing a 2-oxopiperidine-6-carbonyl radical, ($N^\pi$-Me)His, a 3-methylhistidyl radical and ABH a 2-azabicyclo[2.2.1]heptane-3-carbonyl radical.

10. A compound according to claim 1, which is HomoPyroGlu-Leu-ABH-$NH_2$, its diastereoisomers, enantiomers and epimers, as well as its addition salts with a pharmaceutically acceptable acid, HomoPyroGlu representing a 2-oxopiperidine-6-carbonyl radical, Leu representing a leucyl radical and ABH a 2-azabicyclo[2.2.1]heptane-3-carbonyl radical.

11. A compound according to claim 1, which is PyroGlu-His-ABH-$NH_2$, its diastereoisomers, enantiomers and epimers, as well as its addition salts with a pharmaceutically acceptable acid, PyroGlu representing a 2-oxopyrrolidine-5-carbonyl radical, His representing a histidyl radical and ABH a 2-azabicyclo[2.2.1]heptane-3-carbonyl radical.

12. A compound according to claim 1, which is HomoPyroGlu-His-ABH-$NH_2$, its diastereoisomers, enantiomers and epimers, as well as its addition salts with a pharmaceutically acceptable acid, HomoPyroGlu representing a 2-oxopiperidine-6-carbonyl radical, His a histidyl radical and ABH a 2-azabicyclo[2.2.1-]heptane-3-carbonyl radical.

13. A compound according to claim 1, which is HomoPyroGlu-($N^\tau$-Me)His-ABH-$NH_2$, its diastereoisomers, enantiomers and epimers, as well as its addition salts with a pharmaceutically acceptable acid, HomoPyroGlu representing a 2-oxopiperidine-6-carbonyl radical, ($N^\tau$-Me)His a 1-methylhistidyl radical and ABH a 2-azabicyclo[2.2.1]heptane-3-carbonyl radical.

14. A compound according to claim 1, which is HomoPyroGlu-Leu-MIABO-$NH_2$, its diastereoisomers, enantiomers and epimers, as well as its addition salts with a pharmaceutically acceptable acid, HomoPyroGlu representing a 2-oxopiperidine-6-carbonyl radical, Leu representing a leucyl radical and MIABO a 4-methyl-1-isopropyl-2-azabicyclo[2.2.2]octane-3-carbonyl radical.

15. A compound according to claim 1, which is PyroGlu-($N^\pi$-Me)His-dMABO-$NH_2$, its diastereoisomers, enantiomers and epimers, as well as its addition salts with a pharmaceutically acceptable acid, PyroGlu representing a 2-oxopyrrolidine-5-carbonyl radical, ($N^\pi$-Me)His a 1-methylhistidyl radical and dMABO a 1,4-dimethyl-2-azabicyclo[2.2.2 ]octane-3-carbonyl radical.

16. A pharmaceutical composition containing, as active principle, at least one compound according to claim 1, in combination with one or more pharmaceutically acceptable, non-toxic, inert vehicles or excipients.

17. A method for treating an animal or human living body afflicted with a condition requiring a facilitator of central cholinergic or noradrenergic neurotransmission, comprising the step of administering to the said living body an amount of a compound of claim 1 which is effective for alleviation of the said condition.

* * * * *

UNITED STATES PATENT AND TRADEMARK OFFICE
CERTIFICATE OF CORRECTION

PATENT NO. : 5,098,888

DATED : Mar. 24, 1992

INVENTOR(S) : Michel Vincent, Georges Remond, Bernard Portevin, Yolande Herve, Jean Lepagnol, Catherine Biton It is certified that error appears in the above-identified patent and that said Letters Patent is hereby corrected as shown below:

Title Page [57] ABSTRACT, line 9; "alower"
    should read -- a lower --.
Column 9, approximately line 63; "ABH-N H$_2$" should read
    -- ABH-NH$_2$ --.
Column 16, line 25; "-Me(His-" should read -- -Me)His- --.
Column 17, approximately line 21-15:

Reads " 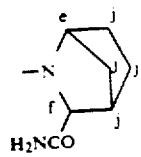    Should -- 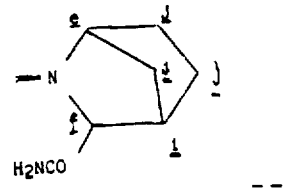
                                Read
 "                                                              --

Column 18, line 6; "isomar" should read -- isomer --.
Column 22, line 23; move the closing parenthesis "]" from the
    beginning of line 23 to the end of line 22 and insert before
    the hyphen.

Signed and Sealed this

Twenty-first Day of December, 1993

Attest:

BRUCE LEHMAN

Attesting Officer    Commissioner of Patents and Trademarks